United States Patent
Oberhoff et al.

(10) Patent No.: US 6,637,270 B1
(45) Date of Patent: Oct. 28, 2003

(54) SYSTEM FOR TRANSMITTING ULTRASONIC WAVES

(75) Inventors: Dietmar Oberhoff, Leichlingen (DE); Günther Coen, Düsseldorf (DE); Ernst Luhn, Haan (DE); Gerhard Lorenz, Krefeld (DE)

(73) Assignee: Betriebsforschungsinstitut VDEh-Institut fur Angewandte forschung GmbH, Duseldorf (DE)

( * ) Notice: Subject to any disclaimer, the term of this patent is extended or adjusted under 35 U.S.C. 154(b) by 0 days.

(21) Appl. No.: 09/198,317

(22) Filed: Nov. 23, 1998

(30) Foreign Application Priority Data

Nov. 25, 1997 (DE) .......................... 197 52 154

(51) Int. Cl.⁷ .................. G01N 29/00; G01N 29/04
(52) U.S. Cl. .................. 73/632; 73/643; 73/626; 73/610
(58) Field of Search .................. 73/579, 596, 602, 73/609, 626, 632, 643, 645, 654, 659, 661, 662

(56) References Cited

U.S. PATENT DOCUMENTS

| 4,058,002 A | | 11/1977 | Moran .......................... 73/620 |
|---|---|---|---|
| 4,289,030 A | * | 9/1981 | Alers et al. .................... 73/643 |
| 4,296,486 A | * | 10/1981 | Vasile .......................... 73/643 |
| 4,307,615 A | * | 12/1981 | Robinson ....................... 73/643 |
| 4,408,493 A | * | 10/1983 | Peterson ....................... 73/643 |
| 4,420,978 A | * | 12/1983 | Robinson et al. ............... 73/643 |
| 5,199,299 A | | 4/1993 | Hughes et al. ................. 73/610 |
| 5,269,189 A | * | 12/1993 | Thompson et al. ............ 73/632 |
| 5,295,485 A | | 3/1994 | Shinomura et al. ..... 128/600.07 |
| 5,566,573 A | * | 10/1996 | Yost ............................. 73/643 |
| 5,653,235 A | * | 8/1997 | Teo .............................. 73/626 |
| 5,811,682 A | * | 9/1998 | Ohtani et al. .................. 73/643 |
| 5,817,024 A | | 10/1998 | Ogle et al. ................... 600/447 |
| 6,104,671 A | * | 8/2000 | Hoyt et al. .................... 367/99 |

FOREIGN PATENT DOCUMENTS

WO   97 01768   1/1997

* cited by examiner

Primary Examiner—Helen Kwok
(74) Attorney, Agent, or Firm—Merchant & Gould P.C.

(57) ABSTRACT

The invention relates to a transmitting system for the generation of ultrasonic waves for testing materials, comprising a controllable signal generator and an ultrasonic transducer, wherein the signal generator and the ultrasonic transducer are arranged in the immediate vicinity of one another, in order to provide a transmitting system for ultrasonic testing which has higher effectiveness and lower manufacturing costs than known transmitting systems.

20 Claims, 1 Drawing Sheet

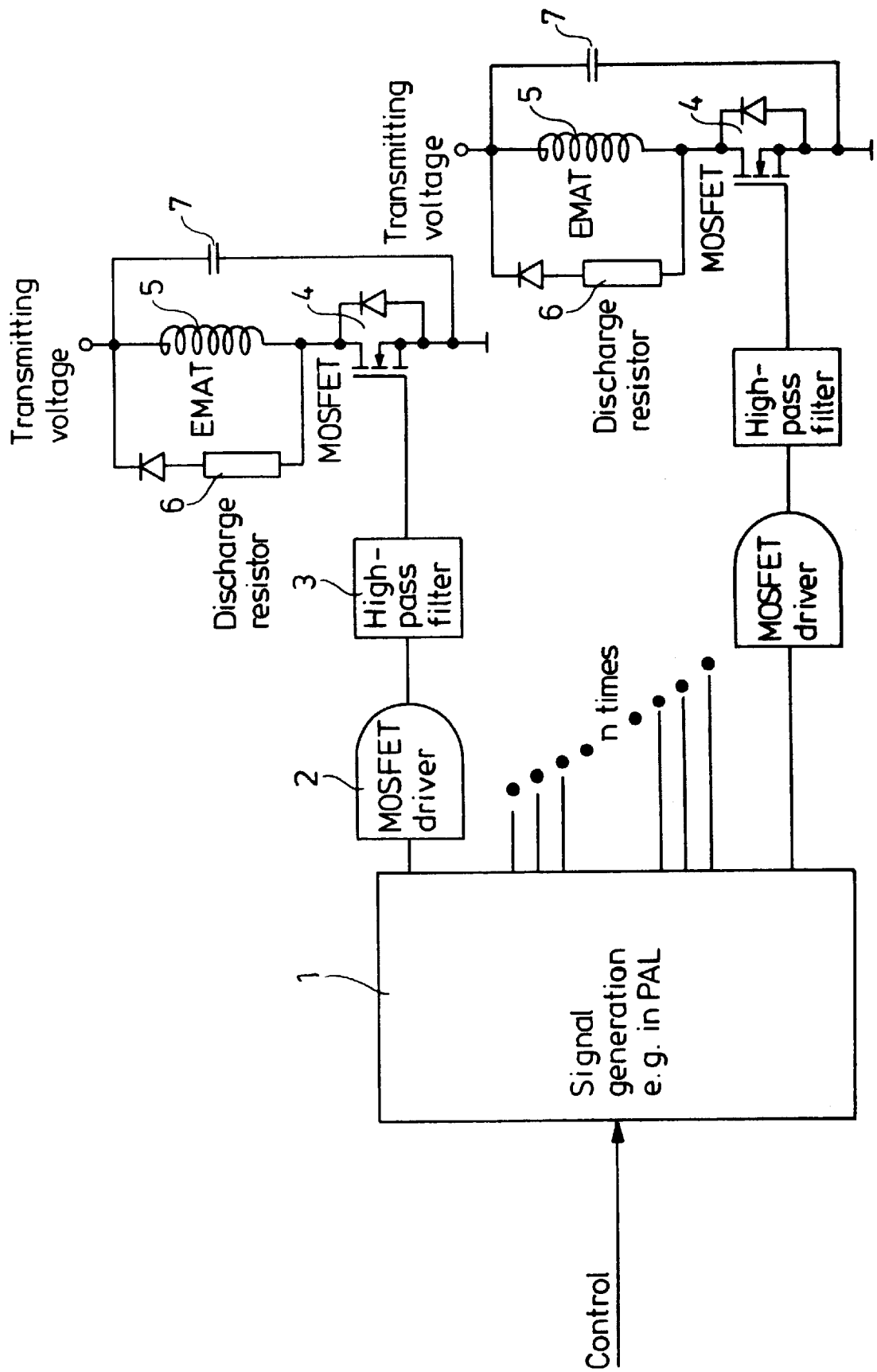

SYSTEM FOR TRANSMITTING ULTRASONIC WAVES

FIELD OF THE INVENTION

The invention relates to a transmitting system for the generation of ultrasonic waves for testing materials.

BACKGROUND OF THE INVENTION

For generating such ultrasonic waves it is known to use a piezoelectric ultrasonic transducer. However, it is a disadvantage of piezoelectric ultrasonic transducers that the transfer of the ultrasonic waves from the piezo generator to the material to be tested requires a coupling medium, since air does not possess sufficiently good transfer properties for use as the transfer medium.

However, the use of a coupling medium interferes with the testing of materials which are moving during testing or of hot materials. In hot or moving material conditions a contactless testing system is necessary or urgently required.

For contactless ultrasonic testing without a coupling medium it is known to use electrodynamic/electromagnetic ultrasonic testing. This depends in its electrodynamic part on the use of the Lorenz force and in its electromagnetic part on the use of the magnetostriction effect to generate ultrasonic waves in the material. The amplitude of the ultrasound produced is proportional to the current density at the surface of the material.

The Lorenz force is generated by inducing an eddy current in the material in a static magnetic field. The metal lattice is thereby excited to an oscillation which is propagated as ultrasonic waves. The characteristics of these ultrasonic waves are determined by the geometry of the transducer and the alternating current frequency of the eddy current.

The alternating current also produces a magnetostriction effect by superimposition of the static magnetic field on the alternating magnetic field. The periodic change in magnetisation produces an ultrasound frequency in a metallic material.

Known transmitters for the production of an electrodynamic/electromagnetic ultrasonic wave consist essentially of two electronic units which are connected together by leads.

A practical ultrasonic examination requires for the transmitting system a transmitter to generate the signal and a transducer to convert the signal into an ultrasonic wave in the test piece. In usual testing systems the transmitting system must be capable of generating a pulse power of about 30 kW at the output of the transmitter, of which about 18 kW is then lost in the feed lines and about 12 kW is available in the transmitting transducer for the generation of ultrasound. In the case of known transmitting systems this can be achieved using transmitters with an AC voltage of about 250 volts by producing in the test piece, by means of a unidirectional transducer with transmitting coils each offset by a distance of a quarter wavelength ($\lambda/4$ spacing), by a phase shift, a superimposition effect and thus an amplification of the ultrasonic waves in one direction of radiation and a cancellation in the other direction of radiation.

Using transmitters of about 250 volt AC a test piece pulse power of about 30 kW can thus be achieved with which an ultrasonic measurement is possible with a corresponding receiver. The maximum transmitting voltage is however limited by the electrical breakdown strength of the transducer. As transducers wound enamelled copper wire coils are used which must be matched to the internal resistance of the system. It is usual to use coils with an impedance of about $10\Omega$. The coil impedance is then in the impedance range of the usual leads connecting the transmitter and the transducer.

To generate the transmitter voltage of 250 volts AC, in the prior art standard 19-inch plug-in units are provided in corresponding switchgear cabinets. The transmitters are connected to the transducer by cables. In the transducer region transducer electronics with corresponding capacitances are required for amplification and compensation for parasitic impedances. In practice a transducer electronic unit is mounted separately from the transmitter in the region of the test piece; and is connected by cables on the one hand to the transmitter and on the other hand to the transmitting coil, which is mounted directly above the test piece.

The high output voltage of 250 volt is already required by reason of the high power loss through the connecting cables between the transmitter circuit board, the transducer electronics (front end electronics) and the transducer. In the case of the usual high transmitter power the high impedance of the transmitting system is thus of consequence for the selection of a suitable transmitter.

To lower the transmitter power required, attempts have long been made to shorten the leads by suitable arrangement of the transducer electronics and of the switchgear cabinets with the transmitter circuit boards. However, because of the constructional conditions, for example in a rolling mill train, in the case of the usual kind of transmitter with the corresponding high voltage, on safety grounds switchgear cabinets—and hence a minimum distance from the test piece—are necessary, and the switchgear cabinets must again be kept some distance away from the rolling mill train in order to avoid interference with the electronics and adverse effects on the electronics of the pickle liquid used in the rolling mill train.

Furthermore the dimensions of the switchgear cabinets, which in addition to the transmitter electronics also have to accommodate the usual binade or decade capacitors consisting in part of 48 European standard circuit boards for exact adjustment of the capacity of the transmitting system, lead to difficulties in positioning. However, the binade capacitors are again necessary for compensation and adjustment of the impedance of the transmitting system.

Further difficulties arise from the fact that the oscillating circuit for amplification of the signal only effects a clean constructive interference when there is precise pulse generation: with known transmitters, however, exact pulse generation is not achieved because of a phase shift caused by impedance of the leads

SUMMARY OF THE INVENTION

The object of the invention is thus to provide a transmitting system for ultrasonic testing which has higher effectiveness and lower production costs than known transmitting systems.

The object is achieved by a transmitting system in which the transmitter, the amplifier and the transducer are not matched to the impedance of the electrical lead, but the impedance of the transmitting system is matched to the amplifier and thereby full advantage is taken of its parameters.

The invention is based on the idea of increasing the power output of the transmitting system by avoiding the lead impedance and thereby overcoming the prejudice that a particular length of lead between the transmitter and transducer is unavoidable. For it is just the shortened lead which permits the use of a smaller transmitting system, which again permits a further shortening of the lead, since with sufficient miniaturisation it becomes possible to mount the transmitter directly beside the transducer.

A further considerable advantage of eliminating the long leads in the transmitting system in accordance with the invention is that the phase shift caused by the leads is very largely avoided, and in connection with a preferably digital transmitting technique a substantially exact pulse amplification is achieved. Thus a clean implementation of the constructive interference can be achieved.

By matching the impedance of the transducer segments to the power switches optimum advantage can be taken of their parameters. The shortened leads are no longer of any electronic consequence. A standard power MOSFET (75 V, 240 A) can be used at a transducer segment impedance of $0.3125\Omega$, so that 18 kW can be achieved in the transducer with a transmitter segment at 75 V. The impedance of the multicore cable used (length of lead about 10 mm) is negligible. For a transmitter comprising 12 segments, there is a total pulse power of 216 kW, which is available in the transmission transducer without lead losses for the generation of ultrasound. This results in a power gain of the transmitting system by a factor of 17.8 or an increase in the ultrasound amplitude of, for example, 25 dB at 456 kHz.

The transducer is preferably made in the form of a flat printed circuit with flat windings. The transducer circuit board can be adapted to curved surfaces of the test piece by the use of flexible printed boards. Alternatively, however, a composite transducer made up of segmented coils of enamelled copper wire can be used.

It is preferred to use as the transmitter a quartz-controlled PAL. Alternatively, however, other signal-generating electronic devices of the smallest possible size, such as, for example, ASICs, can be used, and discrete circuits can also be incorporated in the device of the invention.

The preferred use of integrated circuit devices for the transmitting system permits a further reduction in the size of the circuit boards.

The short leads in the transmitting system of the invention also allow the usual binade capacitors in the form of numerous capacitors which perform the function of compensation of parasitic inductances and in known transmitting systems, even when integrated circuits are used; typically require about three 19-inch plug-in units with 48 European standard circuit boards, to be dispensed with, since the parasitic inductances are substantially all attributable to the leads which are not needed when using the invention. The transmitting system in accordance with the invention is thus not only substantially smaller than known transmitting systems, but also requires considerably fewer components. The small size also makes it possible to take protective measures against harmful effects of the rolling mill train, for example encapsulation of the circuit in synthetic resin.

The smaller the size of the transmitting system, the more extensive are the possibilities for the use of a transmitting system which, through its proximity to the ultrasonic transducer, is consequently also mounted in the immediate vicinity of the test piece.

In the preferred embodiment the transducer is directly connected to the power switches.

BRIEF DESCRIPTION OF THE DRAWINGS

The drawing show an exemplary embodiment, with reference to which the invention will now be described in more detail.

DETAILED DESCRIPTION

The ultrasound transmitting system comprises a PAL 1, which is connected to a suitable control unit and generates a programmable pulse pattern to control the power part of the individual transducer segments. By means of the control of the PAL 1 it is further possible to generate a number of signals which is dependent on the desired pulse amplification. The signals are passed through a MOSFET driver 2 and a standard high pass filter 3 to the power MOSFETs 4, which are directly connected to the coil segments 5 of the transducer segments 8.

Each transducer segment 8 forms a discharge circuit with a discharge resistor 6 and a capacitor 7, which effects a continuous voltage build-up and an abrupt discharge for the production of the surface current and the ultrasonic waves in the test piece.

The capacitor 7 is mounted in the vicinity of the coil 5. The resistor 6 is matched to the impedance of the coil 5.

By each of the transducer segments 8 of the transducer mounted at a distance of about 0.6 mm above the test piece shown, an ultrasonic pulse can be generated, which by suitable arrangement of the coils with a $\lambda/4$ offset leads to a clean amplification and unidirectional alignment of the ultrasonic waves by means of the constructive interference.

By the precise signal generation by means of a PAL and precise control of the moment of discharge of the discharge circuit by means of the MOSFETs, the generation of ultrasound becomes so accurate with regard to the phase relation of the interfering individual signals that the known losses which occur in the wave amplification with the use of interference do not occur.

By the use of a printed coil with the embodiment described the internal resistance of the coil can be exactly matched to the output resistance of the MOSFETs (e.g. at 75 V and 240 A to exactly $0.3125\Omega$), which permits optimum advantage to be taken of the MOSFETs. With the use of transducers made up of segmented coils of enamelled copper wire the same is true in a general sense, but both the precision of the matching and the reproducibility of the transducer itself are higher in the case of the printed coils.

With the use of transducer coils which are offset by $0\lambda$, $\lambda/4$, $1\lambda$, $5\lambda/4$ etc, and control signals which are delayed by 0t, 1t etc and inverted a particularly good radiation characteristic can be obtained.

What is claimed is:

1. A transmitting system for generating ultrasonic waves in a test piece by electrodynamic/electromagnetic ultrasonic conversion which utilizes electromagnetic waves for inducing ultrasonic waves within the test piece, the transmitting system comprising a controllable signal generator and a plurality of transducers wherein the signal generator and each of the plurality of transducers are connected by low impedance leads, and the signal generator and the transducers are located in the immediate vicinity of one another, and wherein signals transmitted between the signal generator and the transducer are not amplified.

2. A transmitting system as claimed in claim 1, wherein the controllable signal generator comprises a PAL or ASIC.

3. A transmitting system as claimed in claim 1, wherein each transducer comprises a printed circuit with flat windings or wire coils.

4. A transmitting system as claimed in claim 1, wherein each said transducer comprises a power switch composed of a field effect transistor.

5. A transmitting system as claimed in claim 1, wherein each transducer comprises a coil with an impedance, and a discharge resistor having a resistance, the resistance of the resistor corresponding to the impedance of the coil.

6. A transmitting system as claimed in claim 5, further including a capacitor, the capacitor being located closely adjacent to the coil.

7. A transmitting system as claimed in claim 1, wherein each said lead has a length of about 10 mm.

8. A transmitting system as claimed in claim 4, wherein the impedance of each transducer is matched to the power switches.

9. A transmitting system for generating ultrasonic waves in a test piece by electrodynamic/electromagnetic ultrasonic conversion which utilizes electromagnetic waves for inducing ultrasonic waves within the test piece, the transmitting system comprising a controllable signal generator and a plurality of transducer segments, wherein the signal generator and the transducer segments are connected by low impedance leads, and the signal generator and the transducer segments are located in the immediate vicinity of one another, and wherein an impedance of the transducer segments is such that a total pulse power available to a transmission transducer is substantially equal to the power applied to the transducer segments multiplied by the number of transducer segments.

10. A transmitting system as claimed in claim 9, wherein the controllable signal generator comprises a PAL or ASIC.

11. A transmitting system as claimed in claim 9, wherein each transducer segment comprises a printed circuit with flat windings or wire coils.

12. A transmitting system as claimed in claim 9, wherein each said transducer segment comprises a power switch composed of a field effect transistor.

13. A transmitting system as claimed in claim 9, wherein each transducer segment comprises a coil with an impedance, and a discharge resistor having a resistance, the resistance of the resistor corresponding to the impedance of the coil.

14. A transmitting system as claimed in claim 13, further including a capacitor, the capacitor being located closely adjacent to the coil.

15. A transmitting system for generating ultrasonic waves in a test piece by electrodynamic/electromagnetic ultrasonic conversion, comprising:

a controllable signal generator capable of generating a signal; and at least one transducer segment connected to the controllable signal generator for receiving the signal therefrom and generating an electromagnetic wave for inducing an ultrasonic wave in the test piece, the transducer segment including a power switch connected to the controllable signal generator and controlling transmission of the signal from the controllable signal generator to the transducer segment;

wherein an impedance of the transducer segment is such that a total pulse power available to a transmission transducer is substantially equal to the power applied to the transducer segment multiplied by the number of transducer segments.

16. The transmitting system according to claim 15, wherein the power switch comprises a field effect transistor.

17. The transmitting system according to claim 16, further including a driver and a high-pass filter connected between the controllable signal generator and the field effect transistor.

18. A method of contactless ultrasonic testing of a test piece by electrodynamic/electromagnetic ultrasonic conversion, comprising:

providing a signal generator and a transducer segment positioned closely adjacent to one another and electrically connected to each other by a low impedance lead, the transducer segment including a power switch;

positioning the transducer segment adjacent to but not in contact with the test piece to be tested;

using the signal generator to generate a signal and transmitting the signal to the transducer segment through the low impedance lead and the power switch without amplifying the signal; and generating an electromagnetic wave from the transmitted signal using the transducer segment for inducing an ultrasonic wave in the test piece;

wherein an impedance of the transducer segment is such that a total pulse power available to a transmission transducer is substantially equal to the power applied to the transducer segment multiplied by the number of transducer segments.

19. A transmitting system as for generating ultrasonic waves in a test piece by electrodynamic/electromagnetic ultrasonic conversion which utilizes electromagnetic waves for inducing ultrasonic waves within the test piece, the transmitting system comprising a controllable signal generator and a plurality of transducer segments, wherein the signal generator and the transducer segments are connected by low impedance leads, and the signal generator and the transducer segments are located in the immediate vicinity of one another, and wherein an impedance of the transducer segments is such that a total pulse power available to a transmission transducer is substantially equal to the power applied to the transducer segments multiplied by the number of transducer segments, and wherein each said lead has a length of about 10 mm.

20. A transmitting system for generating ultrasonic waves in a test piece by electrodynamic/electromagnetic ultrasonic conversion which utilizes electromagnetic waves for inducing ultrasonic waves within the test piece, the transmitting system comprising a controllable signal generator and a plurality of transducer segments, wherein the signal generator and the transducer segments are connected by low impedance leads, and the signal generator and the transducer segments are located in the immediate vicinity of one another, and wherein an impedance of the transducer segments is such that a total pulse power available to a transmission transducer is substantially equal to the power applied to the transducer segments multiplied by the number of transducer segments, and wherein each said transducer segment comprises a power switch composed of a field effect transistor, and wherein the impedance of the transducer segments is matched to the power switches.

* * * * *